United States Patent [19]

Muenstedt

[11] 4,266,424
[45] May 12, 1981

[54] APPARATUS FOR DETERMINING THE STRESS-STRAIN PROPERTIES OF VISCOELASTIC MATERIALS IN THE MOLTEN STATE

[75] Inventor: Helmut Muenstedt, Wachenheim, Fed. Rep. of Germany

[73] Assignee: BASF Aktiengesellschaft, Ludwigshafen, Fed. Rep. of Germany

[21] Appl. No.: 15,617

[22] Filed: Feb. 27, 1979

[30] Foreign Application Priority Data

Mar. 21, 1978 [DE] Fed. Rep. of Germany ....... 2812275

[51] Int. Cl.³ ............................................. G01N 3/08
[52] U.S. Cl. .................................... 73/15.6; 73/826
[58] Field of Search ................ 73/15.6, 789, 806, 816, 73/817, 826, 831, 837

[56] References Cited

U.S. PATENT DOCUMENTS

| | | | |
|---|---|---|---|
| 2,154,280 | 4/1939 | Nadai et al. | 73/15.6 |
| 2,346,981 | 4/1944 | Manjoine et al. | 73/15.6 |
| 3,404,562 | 10/1968 | MacGlashan, Jr. | 73/15.6 |
| 3,813,919 | 6/1974 | Taniguchi et al. | 73/15.6 |
| 4,019,365 | 4/1977 | Woo | 73/15.6 |
| 4,114,420 | 9/1978 | Browning | 73/826 |

OTHER PUBLICATIONS

Cogswell, "The Rheology of Polymer Melts Under Tension" in Plastics & Polymers (G.B.) 4/68, pp. 109-111.
Bullman, "Extensional Flow of Polystyrene Melt", Rheol. Acta, 4, (1965) pp. 137-140.
Stevenson, "Elongation Flow of Polymer Melts" in Alche Journal vol. 18, #3, 5/72, pp. 540-547.
Shaw, "Extensional Viscosity of Melts Using a Programmable Tensile Testing Machine" in Proc. 7th Int. Congr. Rheol. 304 (1976).
Vinogradov et al., "Extension of Liquids" in Journal of Polymer Science, vol. 8 (1970) pp. 1-17.

*Primary Examiner*—Herbert Goldstein
*Attorney, Agent, or Firm*—Keil & Witherspoon

[57] ABSTRACT

Apparatus for determining the stress-strain characteristics of materials in the viscoelastic state, especially polymer melts, in which a bar-shaped test specimen arranged vertically in a thermostable bath is stretched by means of a tape attached to a motor-driven reel and the tensile forces are continuously measured by a load cell arranged below the specimen and within the bath.

2 Claims, 5 Drawing Figures

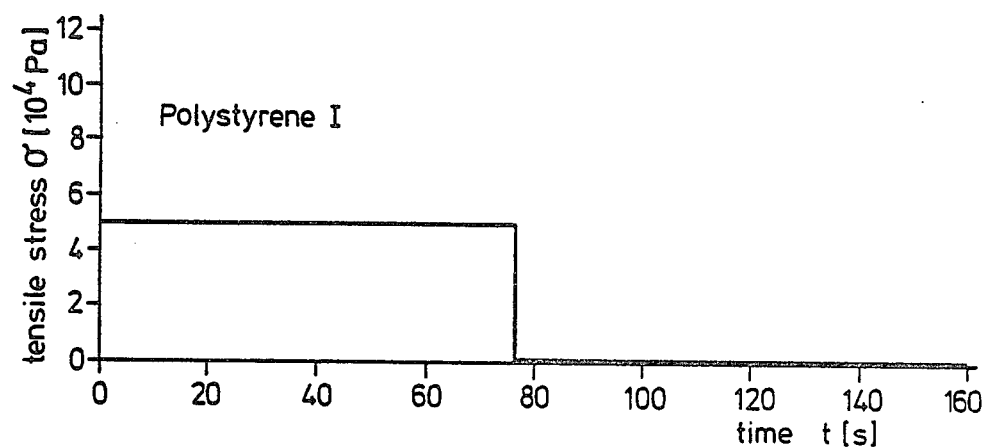
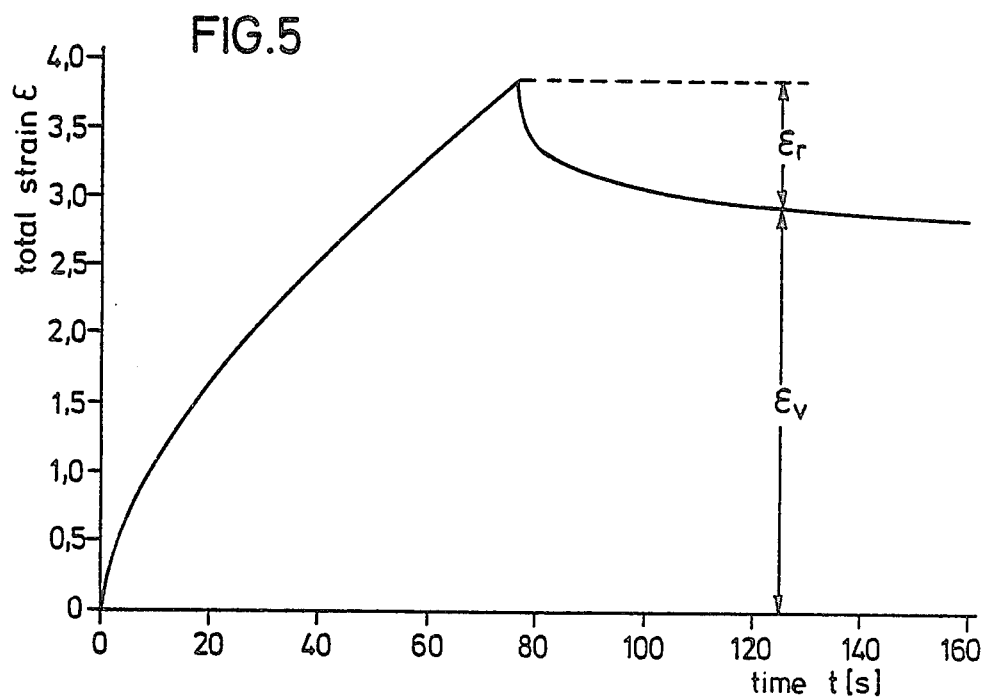
FIG.5

APPARATUS FOR DETERMINING THE STRESS-STRAIN PROPERTIES OF VISCOELASTIC MATERIALS IN THE MOLTEN STATE

The invention relates to an apparatus for determining the stress-strain properties of viscoelastic materials, especially polymer melts, in which a bar-shaped test specimen arranged vertically in a thermostatable bath is stretched by means of a tape attached to a motor-driven reel and the tensile forces are continuously measured by a load cell arranged below the specimen in the direction of pull or, more specifically, in the center line of the pulling assembly.

It is known to investigate the stress-strain characteristics of a material by the following method: A bar-shaped specimen is fastened between two grips which are drawn apart at a predetermined velocity, the tensile force being recorded as a function of time. From the tensile force the tensile stress can be ascertained so that the stress-strain diagram can be drawn. Since, with a constant rate of relative motion of the grips (hereinafter usually referred to as "testing speed"), the stretching rate, which is based on the length of the specimen, decreases as the elongation of the specimen increases, such a method of testing can only be used in the case of small total deformations or if the stress-strain properties of the specimen are independent of the stretching rate. To keep the stretching rate constant it is necessary to use elaborate control equipment.

In the testing of viscoelastic liquids, whose stress-strain characteristics are dependent on time and stress, what has to be done, under defined physical conditions, is either to use a given constant stretching rate and measure the resulting tensile stress or to use a given constant tensile stress and measure the elongation as a function of time.

In order to be able to achieve the object of the invention indicated below, the following rheological relationships have to be considered:

Since in the testing of the stress-strain properties of polymer melts considerable elongation occurs, the changes in length dl of the test specimen should advantageously be expressed with reference to the length at any time, $l$, (according to Hencky) and not with reference to the original length $l_o$ (according to Cauchy). In respect of Hencky strain the following relationships apply:

$$d\epsilon = \frac{dl}{l} \text{ or } \epsilon = \int_{l_o}^{l} 1/l \, dl = \ln l/l_o \quad (1)$$

and $$\dot{\epsilon} = \frac{d\epsilon}{dt} = \frac{1}{l} \frac{dl}{dt} = v/l \quad (2)$$

where v is the testing speed.

The marked elongation which occurs results in a considerable decrease in the cross-sectional area A of the specimen. In the case of incompressible viscoelastic liquids, the tensile stress $\delta$ as a function of the specimen length at any time, $l$, is given by $$\sigma = \frac{F}{A} = \frac{F \cdot l}{A_o \cdot l_o} \quad (3)$$

where F is the tensile force applied to the specimen and $A_o$ is the original cross-sectional area of the specimen.

A constant strain rate according to (2) can be achieved by controlling the testing speed v in accordance with the specimen length $l$ in such a way that $v/l$ is constant. Suitable prior art apparatuses involve the use either of a commercial speed-controlled tensile testing machine or of specially developed testing equipment (such as those apparatus disclosed in R. L. Ballman, Rheol. Acta 4:137 (1965); J. F. Stevenson, A. I. Ch. E. J. 18:540 (1972); M. T. Shaw, Proc. 7th Int. Cong. Rheol., Göeborg, 304 (1976); and G. V. Vinogradov et al., J. Polym. Sci. Pt. A-2 8:1 (1970)). When using a tensile testing machine it should be borne in mind that a specimen in the molten state may be deformed under the action of its own weight and that such testing methods are therefore confined to materials of high viscosity.

The small cross-sectional areas resulting from large elongations lead to small forces, the accurate measurement of which places high requirements on the load measuring system with regard to its resolution and long-term stability. In the case of another prior art apparatus a constant stretching rate is achieved by means of two pairs of wheels resembling sprocket wheels, which grip the two ends of the specimen and draw it apart at a constant speed of rotation, the elongated length of the specimen being defined by the fixed distance between the two wheel pairs (cf. J. Meissner, Rheol. Acta Bd. 8, Heft 1, S. 78–88, U.S. Pat. No. 3,640,127 and German Published Application DAS No. 1,922,414).

In another prior art apparatus, tensile stress is kept constant by means of a cam disk which changes the lever arm of the force acting on the specimen in such a way that the above relation (3) is complied with (cf. F. N. Cogswell, Plastics and Polymers 109–111 (1968)).

Another problem involved in the measuring of the stress-strain properties of viscoelastic liquids consists in introducing the tensile forces into the test specimen and locating the load cell in a place that is the most expedient one for the reproduction of measured values. For example, plastics flow out of the usual grips of a testing machine because of their high viscous proportion when in the molten state. In the prior art apparatus according to Cogswell, cited above, the grips are therefore cooled to temperatures below the melting point or the glass temperature of the plastics material. As a result, however, temperature gradients are set up in the specimen; since the elongational behavior of polymer melts is markedly dependent on temperature, such gradients lead to inhomogeneous deformation of the specimen and hence to highly inaccurate measurements.

Reliable introduction of the tensile forces is ensured by the wheel pairs of the abovementioned prior art apparatus, but the necessary initial specimen length of about 50 cm requires the use of expensive preparation techniques. This known apparatus is therefore unsuitable for investigating materials of which only a laboratory sample of a few grams is available.

It is an object of the invention to provide reliable application of tensile forces to molten specimens up to temperatures of about 200° C., the temperature to be as uniform as possible over the whole length of the specimen so as to ensure homogeneous deformation. Other objects of the invention are to ensure optimum long-term stability of the load measuring means and to prevent the measurement from being thermally influenced by mechanical force-transmitting members.

The apparatus to be developed for achieving these objects should make it possible to carry out, on small specimens, elongational tests at constant stretching rate or at constant tensile stress, as well as relaxation and recoil tests following the application of various elongational stresses. Another requirement is that it should be possible, under various experimental conditions, to separate the total elongation into a viscous, irreversible portion and an elastomeric, recoverable portion. The weight of the specimen should be compensated as far as possible and a high long-term stability of the load measuring means should be ensured.

On the basis of a prior art apparatus for determining the stress-strain properties of viscoelastic materials, especially polymer melts, in which a bar-shaped test specimen arranged vertically in a thermostable bath is stretched by means of a tape attached to a motor-driven reel and the tensile forces are continuously measured by a load cell arranged in the direction of pull, i.e. in the center line of the pulling assembly, the above objects are achieved by connecting the load cell directly or indirectly to the lower end of the specimen and arranging the load cell inside the bath.

Another feature of the invention is that the load cell is firmly attached to the lower angled portion of a support the upper end of which extends beyond the surface of the thermostable bath and is firmly fixed outside the bath.

These and additional features will be apparent to persons skilled in the art from reading this specification and the claims appended hereto in light of the drawings.

FIGS. 2 through 5 are graphs of typical test results achieved using apparatus in accordance with this invention, FIGS. 2 and 3 referring to elongational tests, FIG. 4 to a relaxation test and FIG. 5 to a recoil test.

Figure 1:
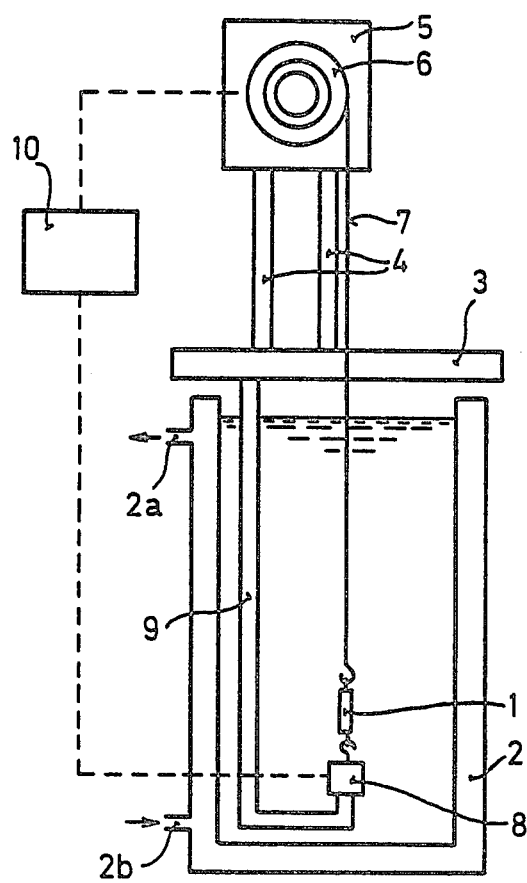
FIG. 1 is a schematic depiction of an embodiment of apparatus according to the invention for carrying out measurements in accordance with the features and objects of the invention set forth above.

The measurements on a specimen 1 are effected in a conventional double-walled vessel 2 provided with connections 2a, 2b for passing a thermal fluid through the space between the two walls. The interior of the vessel contains an oil bath which is inert to the specimen and whose density can be adjusted, preferably a silicone oil. The density of the bath can be so adjusted that the specimen 1 is virtually unaffected by any forces and therefore cannot be deformed under the action of its own weight. The vessel 2 is closed with a lid 3 which carries, in spaced relationship defined by supports 4, the driving motor 5, which is preferably a high-speed servomotor, for driving a reel 6. A pulling tape 7 is fastened to this reel; the free end of the tape is connected in an appropriate manner to the specimen 1, which is to be stressed in a vertical direction. The connection between the specimen 1 and the tape 7 must be such that it does not influence the result of the measurement.

The lower end of the specimen 1 is similarly connected to a load cell 8, which continuously measures the tensile force exerted by the motor-driven reel 6. The load cell 8 is arranged in a fixed position in the thermostated oil bath by means of a support 9, of which the upper end is firmly attached for example to the lid 3 and the lower, angled end carries the load cell.

In order to keep heat dissipation from the thermostated oil bath to a minimum, the support 9 consists of glass or a similar thermally insulating material having a high modulus of elasticity. Since the load cell 9 is located in the thermostated oil bath, the long-term stability of the load cell, i.e. of the most important sensing element, is increased as a result of the oil-bath temperature being constant. The absence of any orifices near the specimen for leading measuring lines from the interior of the vessel 2 to the outside and the resulting effective thermostating of the support 9 ensure optimum temperature constancy along the vertical center line of the pulling assembly, which is a prerequisite for homogeneous deformation of the specimen 1. Location of the load cell 8 directly below the specimen 1 is also of advantage for a stable control of the direct drive of the tape 7 by the motor 5 via the reel 6.

As has been mentioned above, the connection that is the most favorable from the point of view of measuring technology should be chosen for fastening one end of the specimen 1 to the tape 7 and the other end to the load cell 8. During trial operation of the measuring apparatus according to the invention it was found that these connections with the specimen are best produced by means of commercial adhesives, e.g. adhesives which have proved to be suitable at temperatures of up to about 215° C.

Figure 2:
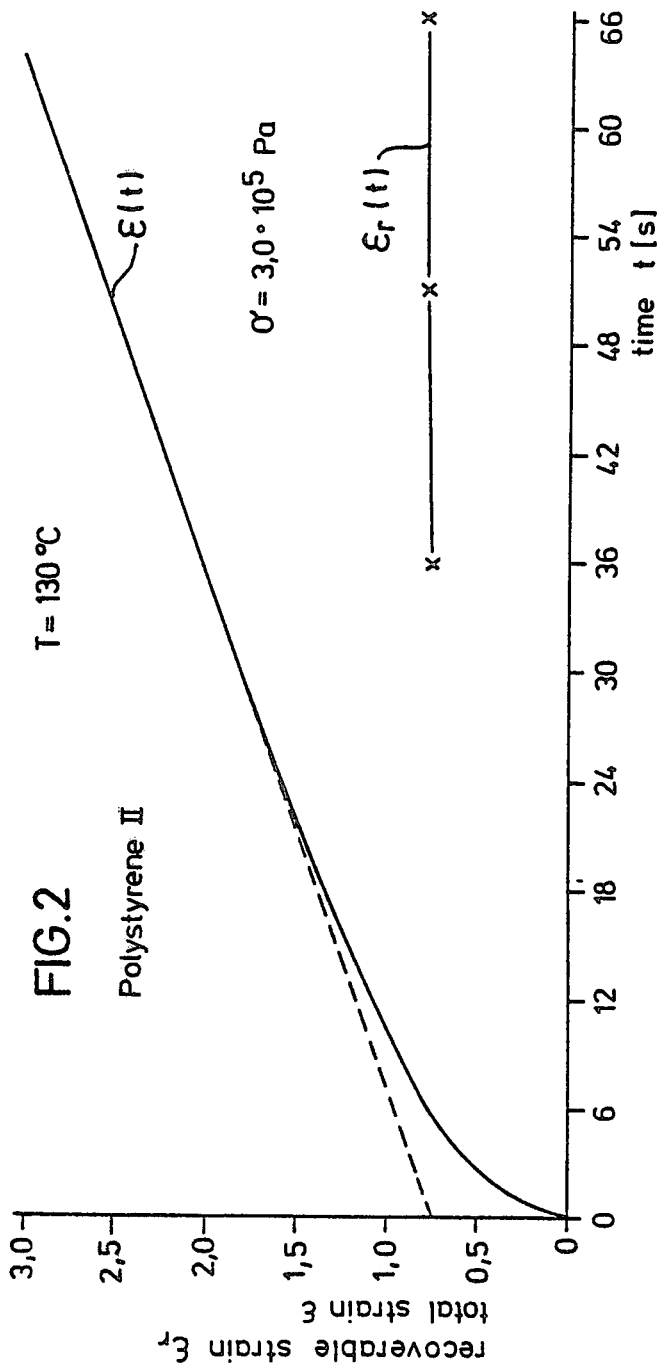
Figure 3:
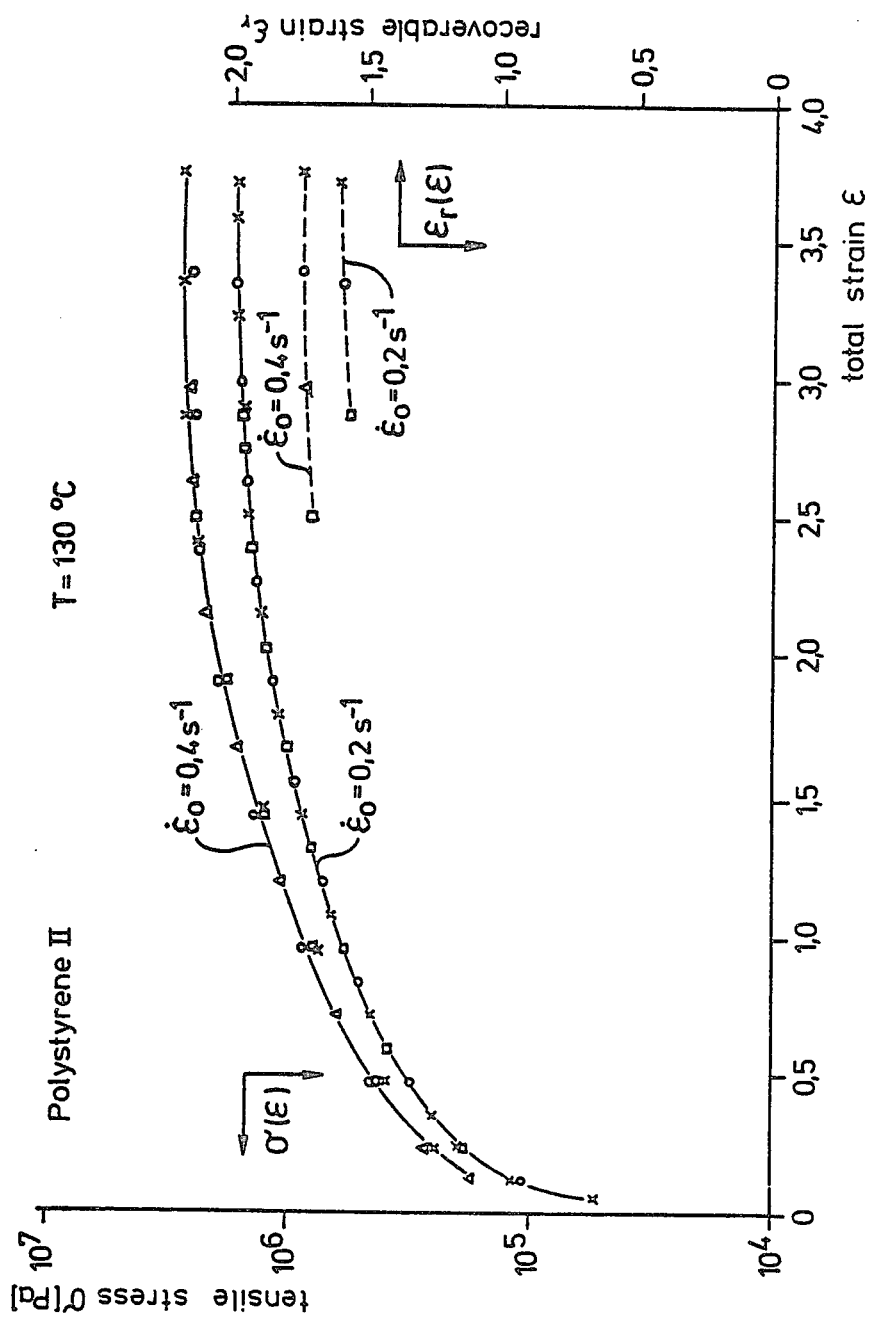

The changes in the length of the specimen 1 are measured via the rotation of the reel 6 and recorded as a function of time. By means of an electronic control system 10 arranged between the load cell 8 and the driving motor 5, the motor 5 can be controlled in such a way that the specimen is deformed either at a constant tensile stress $\delta$ or at a constant stretching rate $\dot{\epsilon}$. The resulting variable is the elongation $\epsilon$ or the tensile stress $\delta$, respectively, either being recorded as a function of time. FIG. 2 is a typical example of an elongational test carried out on a polymer melt at $\delta = 3.10^5$ Pa (pascal), while FIG. 3 reflects a test carried out at $\dot{\epsilon}_o = 0.2$ s$^{-1}$ and $\dot{\epsilon}_o = 0.4$ s$^{-1}$.

Figure 4:
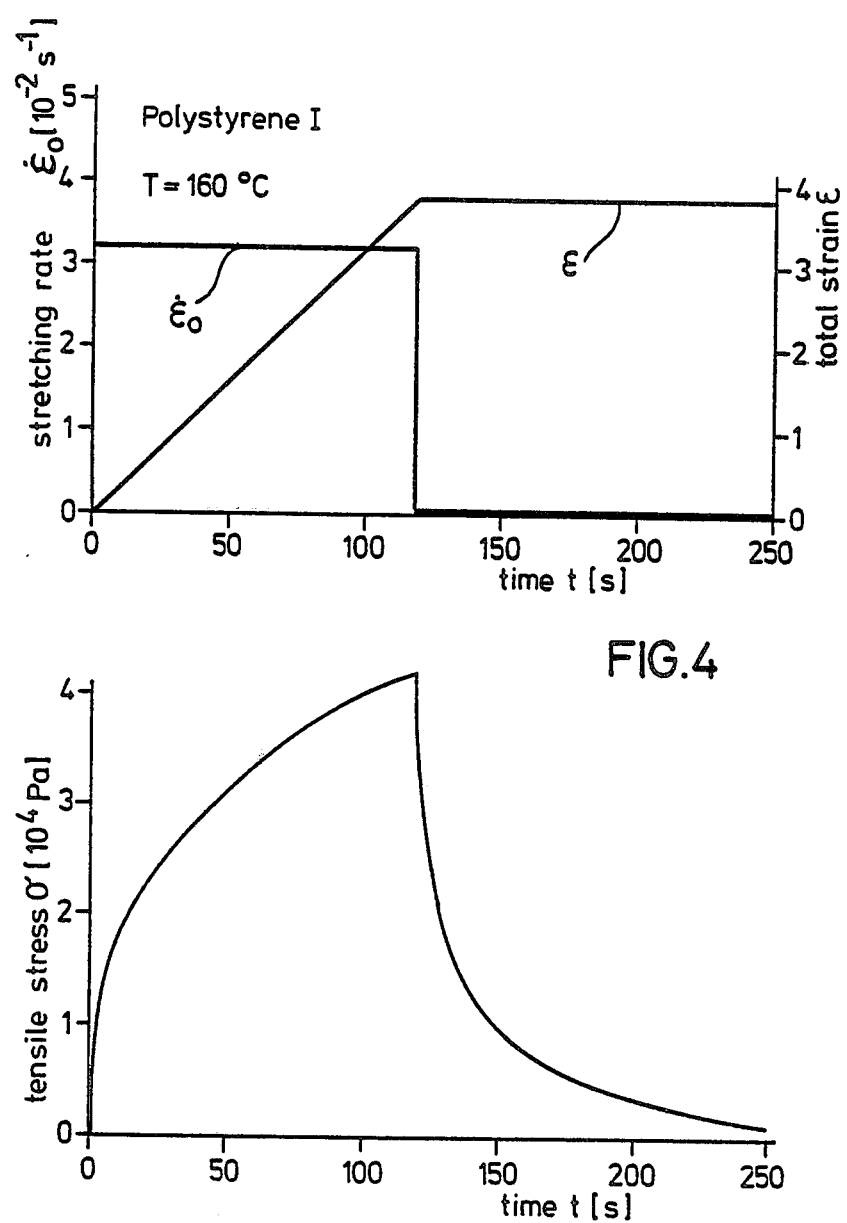

Following any test that can be carried out with this apparatus it is possible to stop extension at any stage of deformation of the specimen and to record the stress as a function of time. Such a test is referred to as a relaxation test. A typical example of such a test is shown in FIG. 4.

A test known as recoil test can be carried out by setting the tensile stress to zero at any stage of deformation of the specimen and measuring the resultant decrease in length of the specimen as a function of time. A typical curve obtained in such a test is shown in FIG. 5.

The apparatus described above also makes it possible to subject the specimen 1 to deformation at a tensile stress $\delta$ or stretching rate $\dot{\epsilon}$ that varies with time. Examples are deformation tests at strains, stresses and stretching rates on which a step function is superposed or tests in which an additional oscillatory portion is superposed on a constant set-point value (tensile stress or stretching rate).

Moreover, the measuring apparatus can be used for separating total strain into a viscous, irreversible portion and an elastomeric, recoverable portion. According to a process disclosed in J. Meissner, *Rheol. Acta*, cited above (see also U.S. Pat. No. 3,640,127), this can be done by cutting the stretched specimen 1 and measuring the remaining strain. The apparatus according to this invention provides another method by which it is possible to determine the elastomeric recovery as a function of time. This is done, after the stretching operation, by setting the tensile stress to zero and recording the length of the specimen as a function of time. The steady-state value obtained after some time corresponds to the recoverable strain determined in cutting tests.

The homogeneity of specimen deformation, which is important for reliable testing, can be checked by lowering the vessel 2 after completion of a test, removing the solidified specimen from its support and measuring its diameter.

I claim:

1. Apparatus for determining the stress-strain properties of viscoelastic liquid, especially of polymers in the molten state, comprising:

a vessel containing a thermostable liquid bath;

a bar-shaped test specimen of viscoelastic liquid arranged vertically in the bath, so that the bath is inert to the test specimen and has a density adjusted to be virtually equal to the density of the test specimen;

means for heating the bath in the vessel and for maintaining a uniform bath temperature over the length of the test specimen; and means to stretch the test specimen, comprising a tape, one end of which is attached to the upper end of the test specimen and the other end of which is attached to a motor-driven reel, and a load cell which is located in a fixed position inside the bath and is connected directly or indirectly to the lower end of the test specimen, the load cell being arranged so as to measure continuously the tensile forces along the vertical center line of the combination of the test specimen and the means to stretch the test specimen, and the load cell being firmly attached to the lower, angled portion of the support, the upper end of which extends beyond the surface of the thermostable bath and is firmly attached outside the bath.

2. The apparatus of claim 1, wherein the support consists of a material of low thermal conductivity, preferably glass.

* * * * *